United States Patent
Ito et al.

(10) Patent No.: US 10,408,761 B2
(45) Date of Patent: Sep. 10, 2019

(54) SURFACE-ENHANCED RAMAN SCATTERING ELEMENT

(71) Applicant: HAMAMATSU PHOTONICS K.K., Hamamatsu-shi, Shizuoka (JP)

(72) Inventors: Masashi Ito, Hamamatsu (JP); Katsumi Shibayama, Hamamatsu (JP); Takafumi Yokino, Hamamatsu (JP); Masaki Hirose, Hamamatsu (JP); Toshimitsu Kawai, Hamamatsu (JP); Kazuto Ofuji, Hamamatsu (JP); Yoshihiro Maruyama, Hamamatsu (JP)

(73) Assignee: HAMAMATSU PHOTONICS K.K., Hamanatsu-shi, Shizuoka (JP)

( * ) Notice: Subject to any disclaimer, the term of this patent is extended or adjusted under 35 U.S.C. 154(b) by 0 days.

(21) Appl. No.: 14/420,506

(22) PCT Filed: Aug. 9, 2013

(86) PCT No.: PCT/JP2013/071697
§ 371 (c)(1),
(2) Date: Feb. 9, 2015

(87) PCT Pub. No.: WO2014/025028
PCT Pub. Date: Feb. 13, 2014

(65) Prior Publication Data
US 2015/0233831 A1    Aug. 20, 2015

(30) Foreign Application Priority Data

Aug. 10, 2012    (JP) ................................. 2012-178771

(51) Int. Cl.
*B82Y 40/00*    (2011.01)
*G01N 21/65*    (2006.01)

(52) U.S. Cl.
CPC ............ *G01N 21/658* (2013.01); *B82Y 40/00* (2013.01); *G01N 2021/651* (2013.01)

(58) Field of Classification Search
CPC . B82Y 30/00; B22F 1/0044; G01N 2021/651; G01N 21/658; G01N 21/554; G01N 21/03
See application file for complete search history.

(56) References Cited

U.S. PATENT DOCUMENTS 6,967,717 B1 * 11/2005  Boss ...................... B82Y 15/00
                                                        356/301
6,970,239 B2 * 11/2005  Chan ..................... C12Q 1/6825
                                                        356/301

(Continued)

FOREIGN PATENT DOCUMENTS

CN    101281133    10/2008
CN    101319994    12/2008

(Continued)

OTHER PUBLICATIONS

Wells, "Efficient disc on pillar substrates for surface enhanced Raman spectroscopy", Jan. 6, 2011, The Royal Society of Chemistry.*

(Continued)

*Primary Examiner* — Maurice C Smith
(74) *Attorney, Agent, or Firm* — Drinker Biddle & Reath LLP

(57) ABSTRACT

A surface-enhanced Raman scattering element comprises a substrate having a principal surface; a molded layer having a support part formed on the principal surface of the substrate so as to extend along the principal surface and a fine structure part formed on the support part; a frame part formed on the principal surface of the substrate so as to surround the support part and fine structure part along the principal surface; and a conductor layer formed on at least (Continued)

the fine structure part and constituting an optical functional part for generating surface-enhanced Raman scattering; while the fine structure part are formed integrally with the support part.

7 Claims, 10 Drawing Sheets

(56) References Cited

U.S. PATENT DOCUMENTS

| | | | |
|---|---|---|---|
| 7,148,964 B2* | 12/2006 | Cunningham | B01L 3/5085 356/326 |
| 7,483,130 B2* | 1/2009 | Baumberg | G01N 21/658 356/301 |
| 7,876,425 B2* | 1/2011 | Sardashti | G01N 21/03 356/246 |
| 2004/0023046 A1 | 2/2004 | Schlottig et al. | |
| 2006/0146323 A1 | 7/2006 | Bratkovski et al. | |
| 2007/0254377 A1* | 11/2007 | Li | G01N 21/658 436/171 |
| 2008/0073206 A1* | 3/2008 | Nogawa | B01L 3/5025 204/403.01 |
| 2008/0094621 A1 | 4/2008 | Li et al. | |
| 2008/0218761 A1 | 9/2008 | Nishikawa et al. | |
| 2010/0078860 A1* | 4/2010 | Yoneda | B29C 37/0003 264/496 |
| 2010/0195106 A1* | 8/2010 | Ogawa | B82Y 15/00 356/445 |
| 2011/0027901 A1 | 2/2011 | Gaster et al. | |
| 2011/0116089 A1 | 5/2011 | Schmidt et al. | |
| 2011/0166045 A1 | 7/2011 | Dhawan et al. | |
| 2011/0267606 A1 | 11/2011 | Ou et al. | |
| 2011/0267607 A1 | 11/2011 | Hu et al. | |
| 2011/0267608 A1 | 11/2011 | Ou et al. | |
| 2012/0105841 A1* | 5/2012 | Hu | G01N 21/658 356/301 |
| 2012/0120401 A1* | 5/2012 | Valsesia | G01N 21/274 356/445 |
| 2013/0176562 A1* | 7/2013 | Shioi | G01N 21/658 356/301 |
| 2014/0043605 A1 | 2/2014 | Tseng et al. | |

FOREIGN PATENT DOCUMENTS

| | | |
|---|---|---|
| CN | 101400976 | 4/2009 |
| CN | 101529229 | 9/2009 |
| CN | 102282094 | 12/2011 |
| CN | 102483354 | 5/2012 |
| JP | S56-142454 | 10/1981 |
| JP | H05-044867 U | 6/1993 |
| JP | H07-260646 A | 10/1995 |
| JP | 2003-026232 A | 1/2003 |
| JP | 2003-240705 | 8/2003 |
| JP | 2005-337771 A | 12/2005 |
| JP | 2007-530925 A | 11/2007 |
| JP | 2007-538264 A | 12/2007 |
| JP | 2008-519254 A | 6/2008 |
| JP | 2008-196992 A | 8/2008 |
| JP | 2008-268059 A | 11/2008 |
| JP | 2009-025316 A | 2/2009 |
| JP | 2009-047623 A | 3/2009 |
| JP | 2009-103643 A | 5/2009 |
| JP | 2009-222401 A | 10/2009 |
| JP | 2009-222507 A | 10/2009 |
| JP | 2009-236830 A | 10/2009 |
| JP | 2009-544967 A | 12/2009 |
| JP | 2010-506191 A | 2/2010 |
| JP | 2011-021085 | 2/2011 |
| JP | 2011-033518 A | 2/2011 |
| JP | 2011-506916 A | 3/2011 |
| JP | 2011-075348 A | 4/2011 |
| JP | 2011-107032 A | 6/2011 |
| JP | 2011107032 A * | 6/2011 |
| JP | 2011-141265 A | 7/2011 |
| JP | 2011-215021 A | 10/2011 |
| JP | 2012-508881 | 4/2012 |
| JP | 2012-132875 A | 7/2012 |
| JP | 2012-233707 A | 11/2012 |
| JP | 2014-037969 | 2/2014 |
| WO | WO 2002-004951 | 1/2002 |
| WO | WO-2007/149120 A2 | 12/2007 |
| WO | WO 2009/119391 A1 | 10/2009 |
| WO | WO-2010/050203 A1 | 5/2010 |
| WO | WO-2010/090111 A1 | 8/2010 |
| WO | WO-2011/021085 A2 | 2/2011 |
| WO | WO 2011/022093 | 2/2011 |
| WO | WO-2011/040504 A1 | 4/2011 |
| WO | WO 2011/121857 | 10/2011 |
| WO | WO-2012/024006 A2 | 2/2012 |
| WO | WO 2013/015810 | 1/2013 |
| WO | WO-2014/025033 A1 | 2/2014 |
| WO | WO-2014/025034 A1 | 2/2014 |

OTHER PUBLICATIONS

"Q-SERS™ G1 Substrate," Opto Science, Inc. (retrieved on-line on Jul. 5, 2013).
Masahiro Yanagisawa, "Detection of Trace Organic Gas Using Molecular Sensor with Plasmon Antenna," Green Technology, Vo. 22, No. 6, Jun. 10, 2012, pp. 42-47, including at least partial English-language translation.
International Search Report dated Nov. 12, 2013, issued in International Application No. PCT/JP2013/071695.
International Search Report dated Nov. 5, 2013, issued in International Application No. PCT/JP2013/071696.
International Search Report dated Nov. 5, 2013, issued in International Application No. PCT/JP2013/071697.
International Search Report dated Nov. 5, 2013, issued in International Application No. PCT/JP2013/071701.
International Search Report dated Nov. 19, 2013, issued in International Application No. PCT/JP2013/071702.
International Search Report dated Nov. 12, 2013, issued in International Application No. PCT/JP2013/071703.
International Search Report dated Nov. 5, 2013, issued in International Application No. PCT/JP2013/071704.
International Search Report dated Nov. 5, 2013, issued in International Application No. PCT/JP2013/071709.
International Search Report dated Apr. 28, 2014, issued in International Application No. PCT/JP2014/052927.
International Search Report dated May 13, 2014, issued in International Application No. PCT/JP2014/052928.
K. Nakamoto et al., "Arrays of Metallic Nanopillars in Holes for Plasmonic Devices", Retrieved from the Internet: URL: http://www.rsc.org/images/LOC/2011/PDFs/Papers/596_0021.pdf, Oct. 6, 2011, XP055289802.
M. Tomohiko et al., "New localized surface plasmon resonance sensor utilizing nanoimprinting technology", NSTI Nanotechnology Conference and Trade Show-NSTI Nanotech, vol. 1, May 11, 2006, p. 58-p. 61, XP009098538.
W. D. Li et al., "Three-dimensional cavity nanoantenna coupled plasmonic nanodots for ultrahigh and uniform surface-enhanced Raman scattering over large area", Optics Express, vol. 19, No. 5, Feb. 14, 2011, p. 3925-3936, XP002751299.
W. Zhang et al., "Giant and uniform fluorescence enhancement over large areas using plamonic nanodots in 3D resonant cavity nanoantenna by nanoimprinting", Nanotechnolgy, vol. 23, No. 22, May 10, 2012, p. 225301, XP020224099.
S. M. Wells et al., "Efficient disc on pillar substrates for surface enhanced Raman spectroscopy", Chemical Communications—Chemcom, vol. 47, No. 13, Jan. 1, 2011, p. 3814-p. 3816, XP055289549.
U.S. Office Action dated Oct. 14, 2016 that issued in U.S. Appl. No. 14/420,510 including Double Patenting Rejections on pp. 2-14.
English Machine Translation of JP 2011-107032, Nishikawa et al., Jun. 2, 2011 as attached to U.S. Office Action dated Oct. 14, 2016 in U.S. Appl. No. 14/420,510.

* cited by examiner

Fig.6
(a)
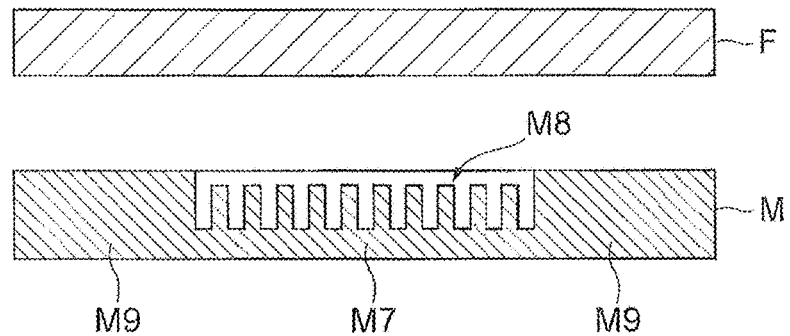
(b)
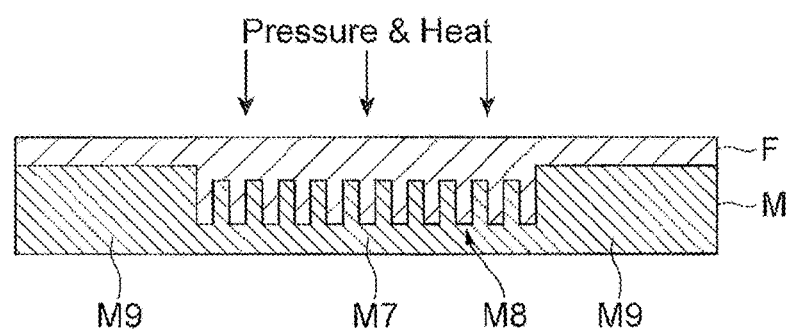
(c)
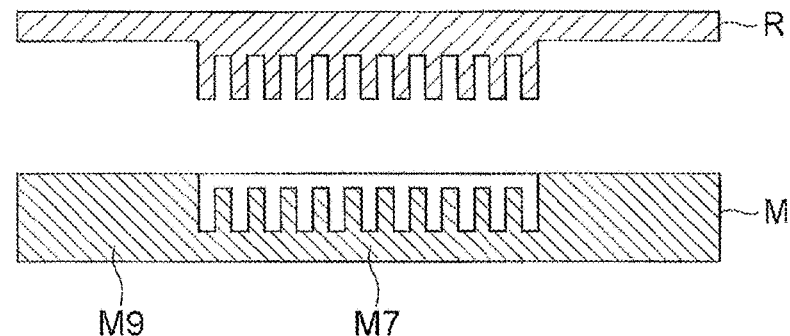

Fig.7
(a)
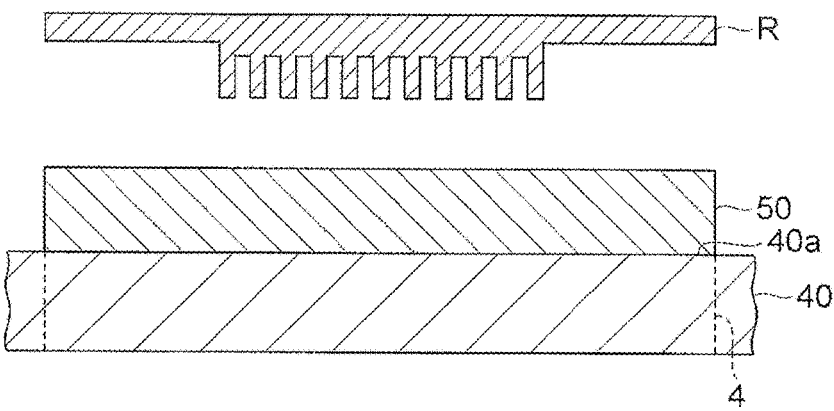
(b)
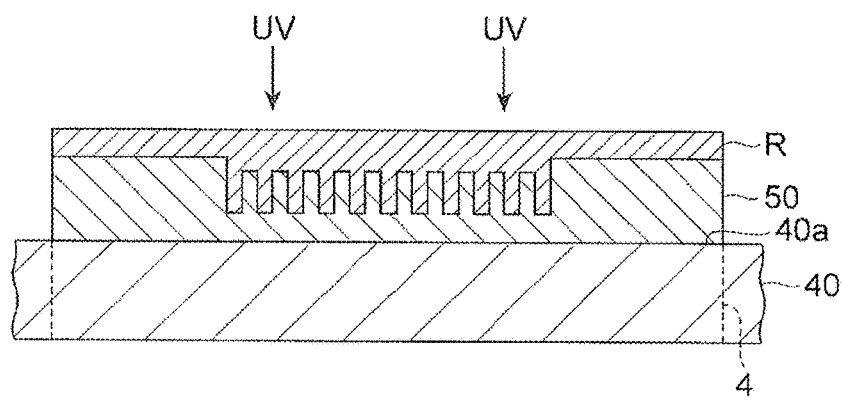
(c)
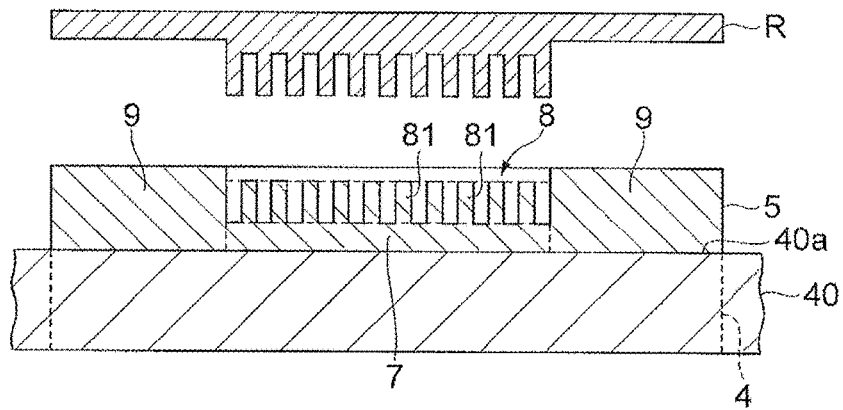

Fig.9
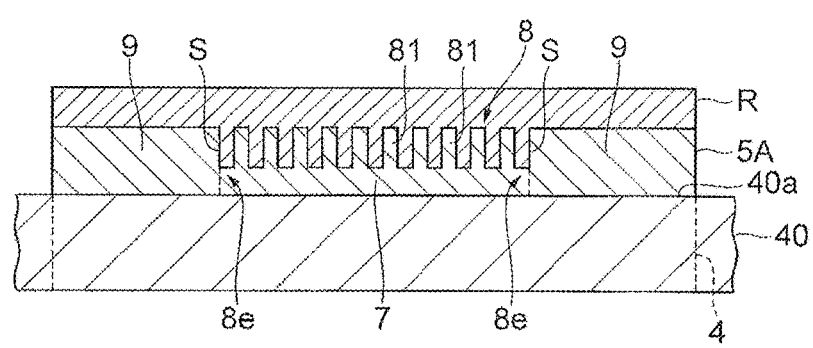
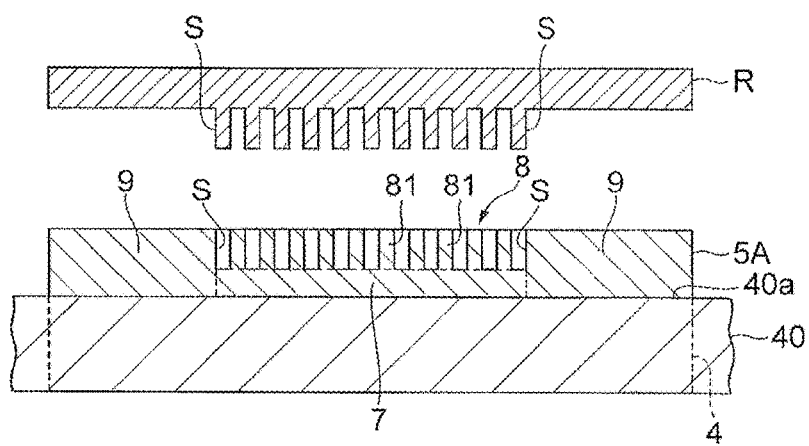

50nm

SURFACE-ENHANCED RAMAN SCATTERING ELEMENT

TECHNICAL FIELD

One aspect of the present invention relates to a surface-enhanced Raman scattering element.

BACKGROUND ART

As a conventional surface-enhanced Raman scattering element, one equipped with a minute metal structure configured to generate surface-enhanced Raman scattering (SERS) has been known (see, for example, Patent Literature 1 and Non Patent Literature 1). In such a surface-enhanced Raman scattering element, when a sample to be subjected to Raman spectroscopy is brought into contact with the minute metal structure and is irradiated with excitation light in this state, surface-enhanced Raman scattering occurs, whereby Raman scattering light enhanced by about $10^8$ times, for example, is released.

Known as examples of the above-mentioned minute metal structure include one manufactured by etching a fluorine-containing silica glass layer and a silica glass film which are sequentially stacked on a silicon substrate, so as to form a plurality of minute projections, and then forming a metal film by sputtering (see, for example, Patent Literature 2) and one manufactured by vapor-depositing $SiO_2$ on a glass substrate so as to form minute columnar bodies and further vapor-depositing Au on top parts of the minute columnar bodies (see, for example, Patent Literature 3).

CITATION LIST

Patent Literature

Patent Literature 1: Japanese Patent Application Laid-Open No. 2011-33518
Patent Literature 2: Japanese Patent Application Laid-Open No. 2009-222507
Patent Literature 3: Japanese Patent Application Laid-Open No. 2011-75348

Non Patent Literature

Non Patent Literature 1: "Q-SERS™ G1 Substrate", [online], Opto Science, Inc., [retrieved on 2012 Jul. 19]. Retrieved from the Internet: <URL: http://www.optoscience.com/maker/nanova/pdf/Q-SERS_G1.pdf>.

SUMMARY OF INVENTION

Technical Problem

However, the minute projections and minute columnar bodies disclosed in Patent Literatures 2 and 3 are constructed separately from the substrate and have such small junction areas with the substrate that they may peel under external forces such as vibrations and shocks and internal forces such as thermal impacts, thereby losing reliability.

In view of such circumstances, it is an object of one aspect of the present invention to provide a surface-enhanced Raman scattering element which can inhibit reliability from lowering.

Solution to Problem

One aspect of the present invention relates to a surface-enhanced Raman scattering element. This surface-enhanced Raman scattering element comprises a substrate having a principal surface; a molded layer having a support part formed on the principal surface of the substrate so as to extend along the principal surface and a fine structure part formed on the support part; a frame part formed on the principal surface of the substrate so as to surround the support part and fine structure part along the principal surface; and a conductor layer formed on at least the fine structure part and constituting an optical functional part for generating surface-enhanced Raman scattering; the fine structure part being formed integrally with the support part.

In this surface-enhanced Raman scattering element, the fine structure part is formed integrally with the support part extending along the principal surface of the substrate. This inhibits the fine structure part from peeling from the substrate. When the fine structure part is formed integrally with the support part extending along the principal surface of the substrate here, a damage to a part of the substrate may affect the whole fine structure part through the support part, for example. However, this surface-enhanced Raman scattering element is equipped with a frame part formed so as to surround the support part and fine structure part. Therefore, the damage is held by the frame part, so as not to affect the fine structure part. Hence, this surface-enhanced. Raman scattering element can restrain the fine structure part from peeling and prevent the damage from affecting the fine structure part, thereby inhibiting reliability from lowering.

In the surface-enhanced Raman scattering element in accordance with one aspect of the present invention, the frame part may be formed integrally with the support part as the molded layer. Even when a sample for Raman spectroscopic analysis is a solution (or a dispersion of a powder sample in a solution such as water or ethanol), this can prevent the sample from leaking out of a boundary between the frame part and support part.

In the surface-enhanced Raman scattering element in accordance with one aspect of the present invention, the frame part may have a height from the principal surface of the substrate greater than that of the fine structure part from the principal surface of the substrate. This enables Raman spectroscopic analysis with a glass cover mounted on the frame part, which makes it possible to conduct the analysis while protecting the fine structure part.

In the surface-enhanced Raman scattering element in accordance with one aspect of the present invention, the frame part may be constituted by an elastic material. This enables the frame part to hold the damage securely.

In the surface-enhanced Raman scattering element in accordance with one aspect of the present invention, the fine structure part may include a plurality of pillars erected on the support part, the plurality of pillars being formed integrally with the support part and connected to each other. This can prevent the damage from affecting each pillar while restraining each pillar from peeling.

In the surface-enhanced Raman scattering element in accordance with one aspect of the present invention, in a direction along the principal surface of the substrate, the frame may have a width greater than a thickness of the pillar. This can securely prevent the damage from affecting each pillar.

Advantageous Effects of Invention

One aspect of the present invention can provide a surface-enhanced Raman scattering element which can inhibit reliability from lowering.

BRIEF DESCRIPTION OF DRAWINGS

FIG. 6 is a diagram illustrating main steps of a method for manufacturing the surface-enhanced Raman scattering unit depicted in FIG. 1;

FIG. 7 is a diagram illustrating main steps of the method for manufacturing the surface-enhanced Raman scattering unit depicted in FIG. 1;

FIG. 9 is a diagram illustrating a part of steps of forming the molded layer depicted in FIG. 8 by nanoimprinting.

DESCRIPTION OF EMBODIMENTS

Figure 1:
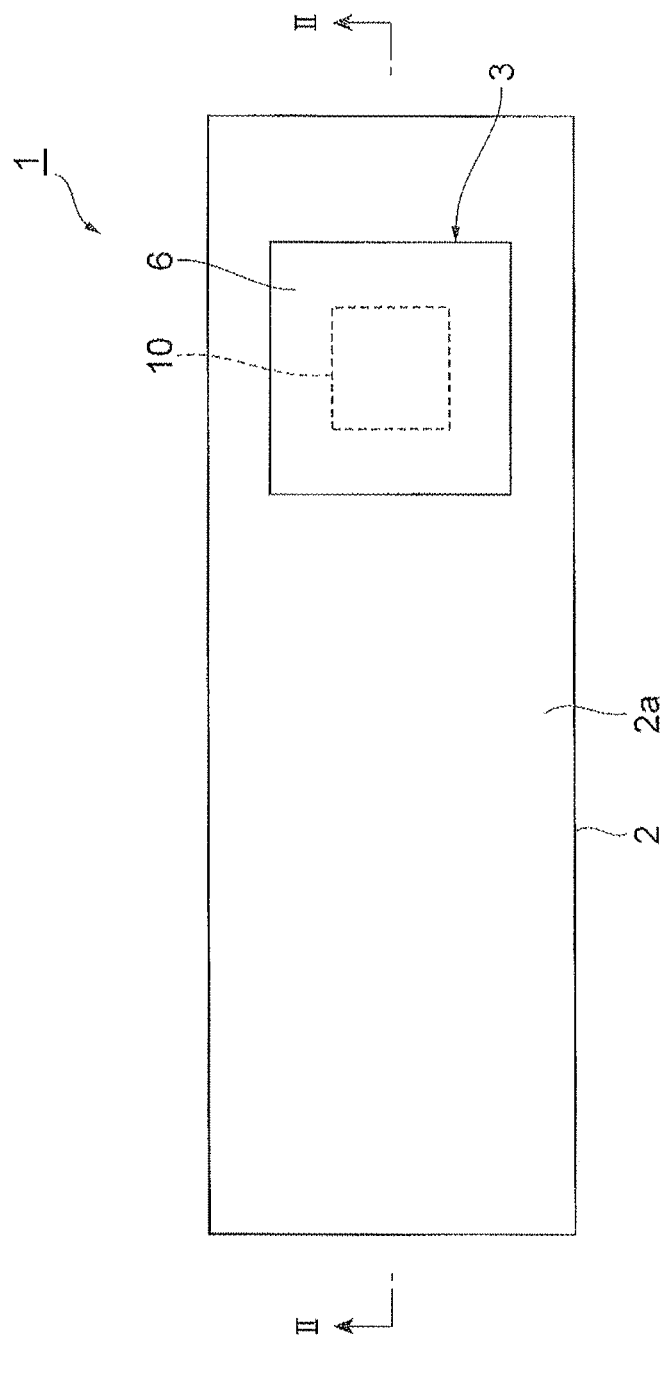
FIG. 1 is a plan view of the surface-enhanced. Raman scattering unit in accordance with an embodiment of the present invention.

In the following, embodiments of the present invention will be explained in detail with reference to the drawings. In the drawings, the same or equivalent parts will be referred to with the same signs while omitting their overlapping descriptions.

Figure 2:
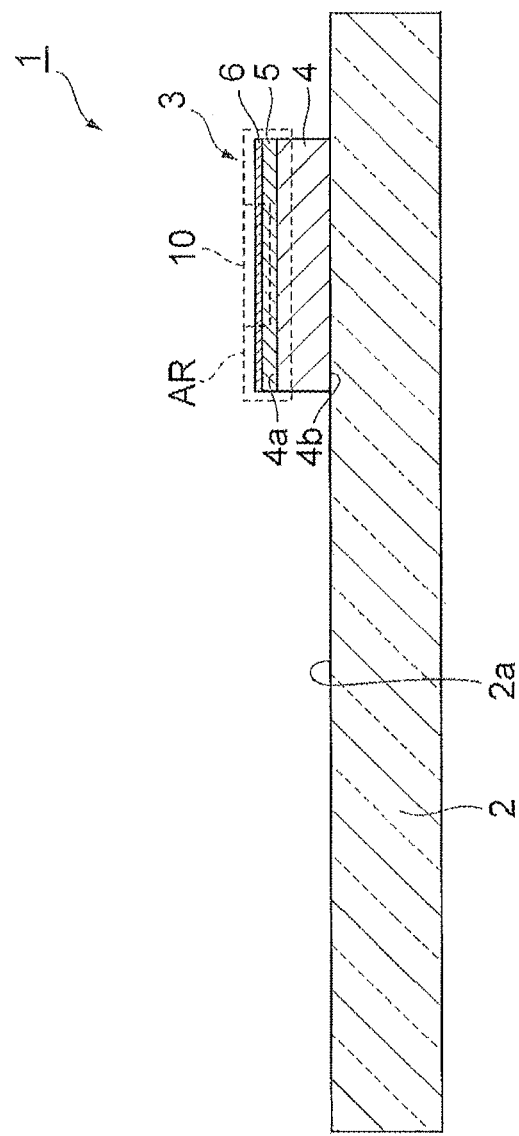
FIG. 2 is a sectional view taken along the line of FIG. 1.

FIG. 1 is a plan view of the surface-enhanced Raman scattering unit in accordance with an embodiment, while FIG. 2 is a sectional view taken along the line of FIG. 1. As illustrated in FIGS. 1 and 2, a SERS unit (surface-enhanced Raman scattering unit) 1 in accordance with this embodiment comprises a handling board 2 and a SERS element (surface-enhanced Raman scattering element) 3 attached onto the handling board 2. The handling board 2 is a rectangular plate-shaped glass slide, resin board, ceramic board, or the like. The SERS element 3 is arranged on a front face 2a of the handling board 2 while being biased to one end part in the longitudinal direction of the handling board 2.

The SERS element 3 comprises a substrate 4 attached onto the handling board 2, a molded layer 5 formed on a front face (principal surface) 4a of the substrate 4, and a conductor layer 6 formed on the molded layer 5. The substrate 4 is formed into a rectangular plate by silicon, glass, or the like and has an outer form on the order of several hundred μm×several hundred μm to several ten mm×several ten mm and a thickness on the order of 100 μm to 2 mm. A rear face 4b of the substrate 4 is secured to the front face 2a of the handling board 2 by direct bonding, bonding with a metal such as solder, eutectic bonding, fusion bonding by irradiation with laser light and the like, anodic bonding, or bonding with a resin.

Figure 3:
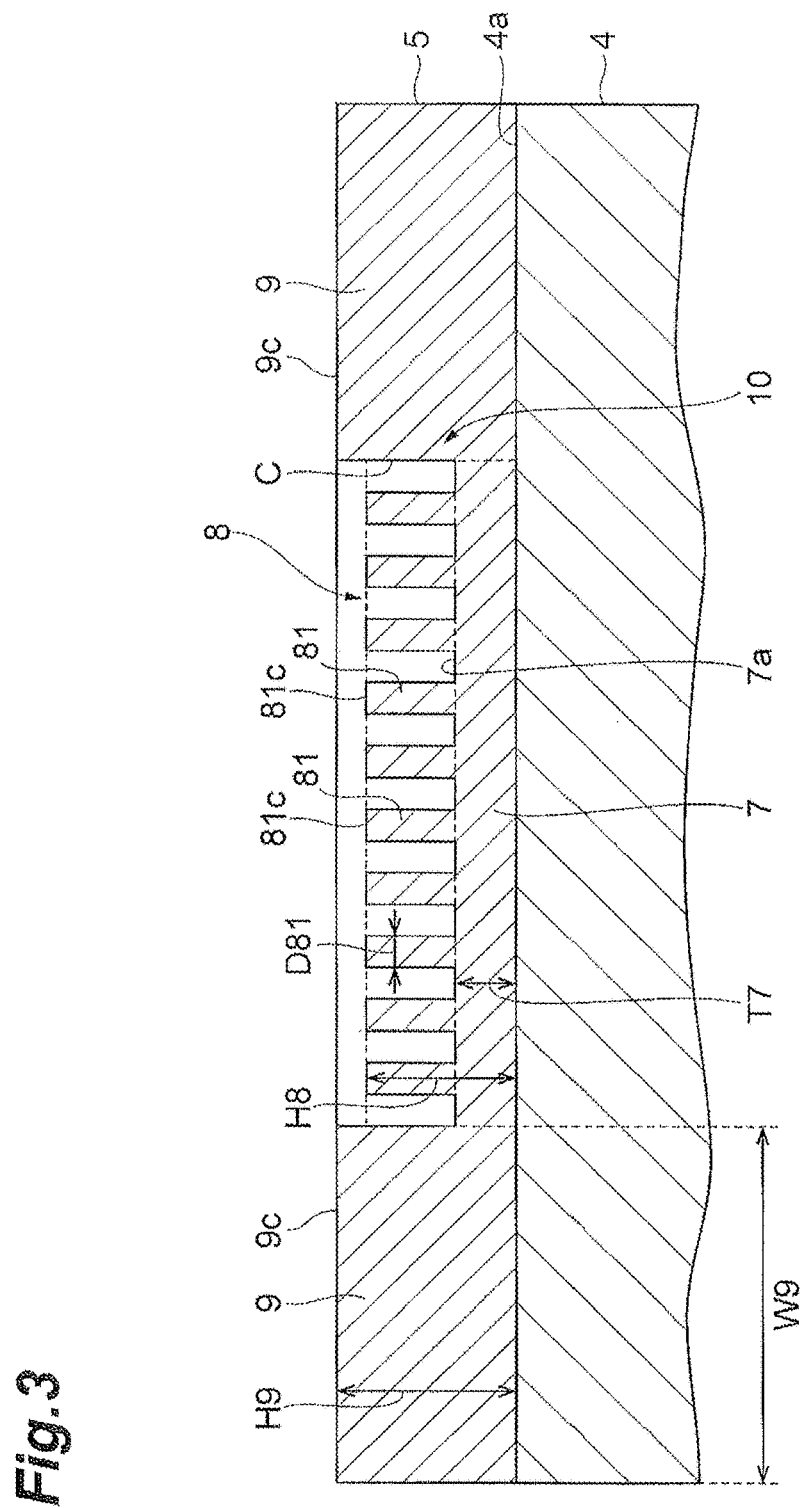
FIG. 3 is a schematic enlarged sectional view of a region AR in FIG. 2.
Figure 4:
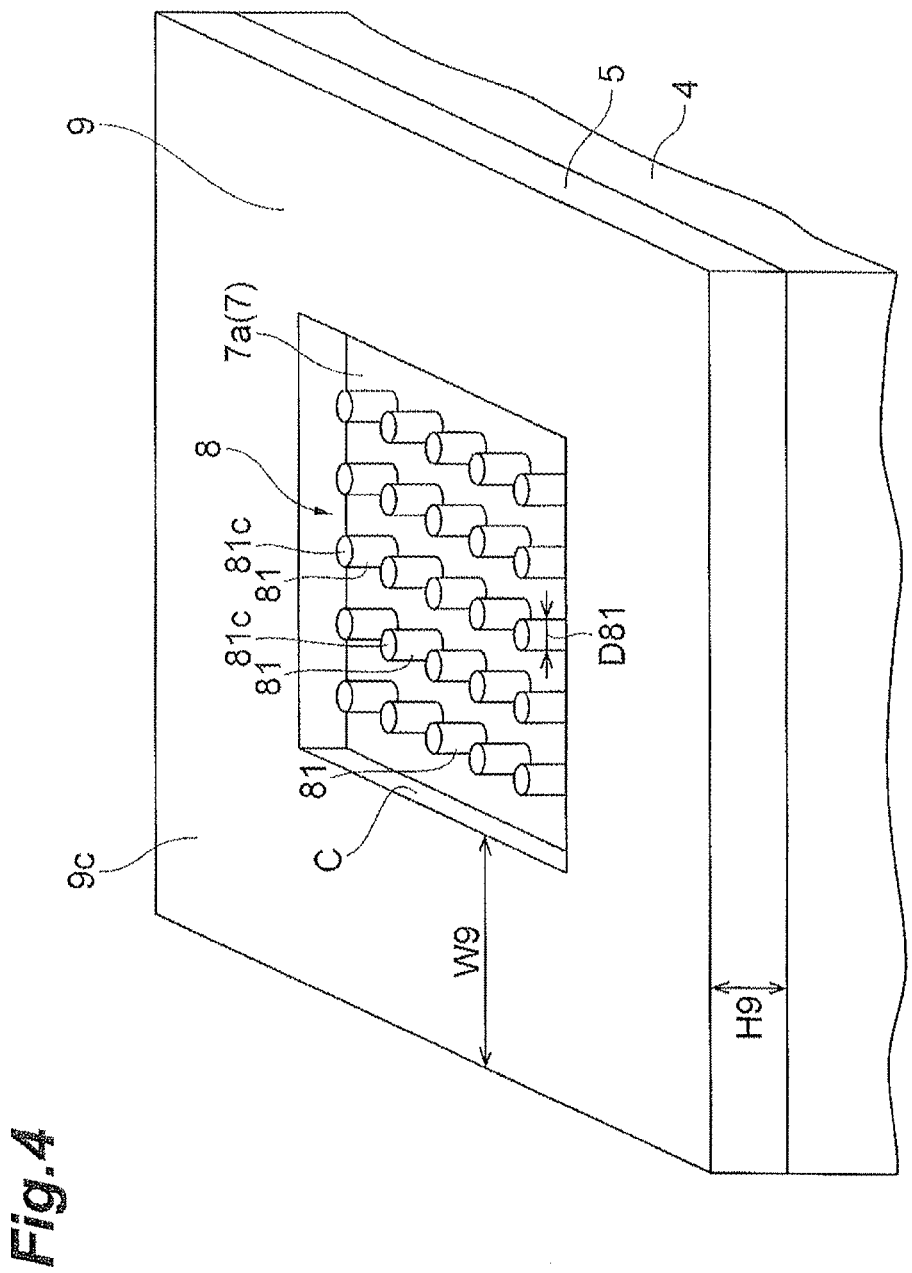
FIG. 4 is a schematic enlarged perspective view of the region AR in FIG. 2.

FIG. 3 is a schematic enlarged sectional view of a region AR in FIG. 2, while FIG. 4 is a schematic enlarged perspective view of the region AR in FIG. 2. FIGS. 3 and 4 omit the conductor layer 6. As illustrated in FIGS. 3 and 4, the molded layer 5 includes a support part 7, a fine structure part 8, and a frame part 9. The support part 7 is a region at substantially the center part of the molded layer 5 and formed on the front face 4a of the substrate 4 so as to extend along the front face 4a. The support part 7 has a rectangular form on the order of several hundred μm×several hundred μm to several ten mm×several ten mm (more specifically on the order of 3 mm×3 mm), for example, when seen in the thickness direction of the substrate 4. The support part 7 has a thickness T7 which is on the order of several ten nm to several ten μm (more specifically about 500 nm), for example.

The fine structure part 8 is formed on the support part 7 at substantially the center part of the molded layer 5. More specifically, the fine structure part 8 includes a plurality of columnar pillars 81 erected on the support part 7 all over the support part 7. Hence, the fine structure part 8 is formed in a rectangular region on the order of several hundred μm×several hundred μm to several ten mm×several ten mm (more specifically on the order of 3 mm×3 mm), for example, when seen in the thickness direction of the substrate 4. The pillar parts 81 may be arranged into a matrix, a triangle, a honeycomb, or the like. The form of the pillar part 81 is not limited to the circular column but may be any of columns, examples of which include elliptical columns and polygonal columns such as quadrangular columns, or any of cones.

The plurality of pillars 81 are formed integrally with the support part 7 and connected to each other. The pillars 81 are periodically arranged at a pitch on the order of several ten nm to several μm, for example, and each have a column diameter and height on the order of several nm to several μm (e.g., 120 nm). A surface 7a of the support part 7 is exposed between the pillars 81 adjacent to each other. Thus, the fine structure part 8 is formed integrally with the support part 7 and has a periodic pattern.

The frame part 9 is a region in an outer peripheral part of the molded layer 5 and is formed into a rectangular ring so as to surround the support part 7 and fine structure part 8 along the front face 4a of the substrate 4. On the front face 4a of the substrate 4, the frame part 9 is continuous from the support part 7 and formed integrally therewith. Therefore, in the molded layer 5, the frame part 9 and support part 7 define a recess C, while the fine structure part 8 is formed on the bottom face of the recess C (the surface 7a of the support part 7).

Here, the frame part 9 has a top part 9c projecting from top parts 81c of the pillars 81 of the fine structure part 8. That is, the frame part 9 has a height (thickness) H9 from the front face 4a of the substrate 4 greater than a height H8 of the fine structure part 8 from the front face 4a of the substrate 4 (the height of the pillar 81 including the thickness T7 of the support part 7) here. The height H9 of the frame part 9 is on the order of several hundred nm to several hundred μm (more specifically about 15 μm), for example. In a direction along the front face 4a of the substrate 4, the frame part 9 has a width W9 on the order of several hundred μm to several mm, for example, which is greater than the column diameter (thickness) D81 of the pillar 81. Here, since the pillar 81 is formed into a circular column, the width W9 of the frame part 9 is made greater than the column diameter D81 of the pillar 81; when the pillar 81 is not formed like a circular column, the width W9 of the frame part 9 can be set greater than the maximum thickness of the pillar 81.

The foregoing molded layer 5 is integrally formed by molding a resin (examples of which include resins based on acrylics, fluorine, epoxy, silicone, and urethane, PET, polycarbonate, and inorganic/organic hybrid materials) or low-melting glass arranged on the front face 4a of the substrate 4 by nanoimprinting, for example.

The conductor layer 6 is formed over the fine structure part 8 and frame part 9. In the fine structure part 8, the conductor layer 6 reaches not only the surfaces of the pillars 81 but also the surface 7a of the support part 7 exposed between the pillars 81. Therefore, on a region of the molded layer 5 formed with the fine structure part 8, the conductor layer 6 has a fine structure corresponding to the fine structure part 8 of the molded layer 5. The conductor layer 6 has a thickness on the order of several nm to several for example.

The conductor layer 6 like this is formed by vapor-depositing a conductor such as a metal (Au, Ag, Al, Cu, Pt, or the like) on the molded layer 5 molded by nanoimprinting, for example, as mentioned above. In the SERS element 3, the conductor layer 6 formed on the fine structure part 8 and the surface 7a of the support part 7 constructs an optical function part 10 which generates surface-enhanced Raman scattering.

Figure 5:
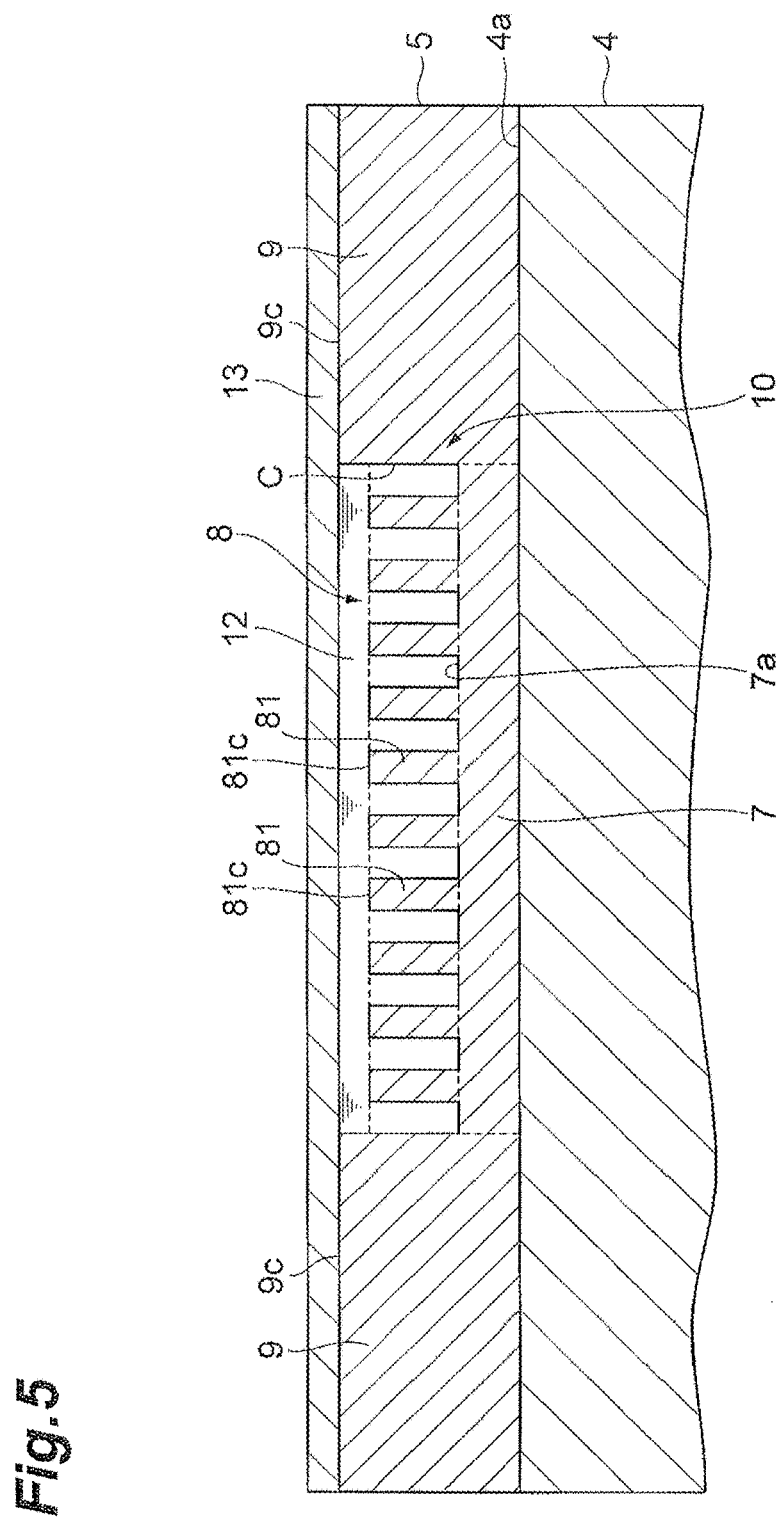
FIG. 5 is a diagram for explaining a method for using the surface-enhanced Raman scattering unit illustrated in FIG. 1.

A method for using the SERS unit 1 will now be explained with reference to FIGS. 1 and 5. FIG. 5 is a schematic sectional view for explaining a method for using the SERS unit depicted in FIG. 1. The conductor layer 6 is omitted in FIG. 5. First, as illustrated in FIG. 1, the SERS unit 1 is prepared.

Subsequently, as illustrated in FIG. 5, a sample 12 of a solution (or a dispersion of a powder sample in a solution such as water or ethanol; the same hereinafter) is dropped with a pipette or the like into the recess C defined by the support part 7 and frame part 9 of the molded layer 5, so as to be arranged on the optical function part 10. Thus, the frame part 9 can be utilized as a cell (chamber) for the solution sample 12. Here, within the recess C, the solution 12 is arranged on the conductor layer 6, which is formed on the surface 7a of the support part 7 and the surfaces of the pillars 81 of the fine structure part 8.

Next, for reducing the lens effect, a glass cover 13 is mounted on the top part 9c of the frame part 9 and brought into close contact with the solution sample 12. Thus, the frame part 9 can be utilized as a mount table for the glass cover 13. Subsequently, the SERS unit 1 is set in a Raman spectroscopic analyzer, and the sample 12 arranged on the optical function part 10 is irradiated with excitation light through the glass cover 13. This generates surface-enhanced Raman scattering at the interface between the optical function part 10 and sample 12, whereby surface-enhanced Raman scattering light derived from the sample 12 is enhanced by about $10^8$ times, for example, and released. Hence, the Raman spectroscopic analyzer enables Raman spectroscopy with high sensitivity and high accuracy.

Not only the above-mentioned method, but the following methods may also be used for arranging the sample on the optical function part 10. For example, while holding the handling board 2, the SERS element 3 may be dipped in and lifted from the solution sample, and then the sample may be blown to dry. A minute amount of the solution sample may be dropped onto the optical function part 10 and left to dry. A powder sample may be dispersed as it is on the optical function part 10.

An example of methods for manufacturing the SERS unit 1 will now be explained with reference to FIGS. 6 and 7. First, as illustrated in (a) of FIG. 6, a master mold M and a film base F are prepared in this manufacturing method. The master mold M has a pattern corresponding to the above-mentioned molded layer 5. More specifically, the master mold M includes a fine structure part M8 corresponding to the fine structure part 8 (including the pillars 81) of the molded layer 5, a frame part M9 corresponding to the frame part 9 of the molded layer 5, and a support part M7 formed integrally with the fine structure part M8 and frame part M9.

Subsequently, as illustrated in (b) of FIG. 6, the film base F is pressurized and heated while being pressed against the master mold M, so as to transfer the pattern of the master mold M to the film base F (thermal nanoimprinting). Thereafter, as illustrated in (c) of FIG. 6, the film base F is released from the master mold M, so as to yield a replica mold (replica film) R having a pattern which is the reverse of the pattern of the master mold M.

Also employable as a method for manufacturing the replica mold (replica film) R is one in which a base (example of which include film bases such as PET and hard bases such as silicon and glass) coated beforehand with a UV-curable nanoimprinting resin (examples of which include resins based on acrylics, fluorine, epoxy, silicone, and urethane and inorganic/organic hybrid materials) is pressurized and irradiated with ITV while being pressed against the master mold M, so as to transfer the pattern of the master mold M to the UV-curable nanoimprinting resin on the base.

Next, as illustrated in (a) of FIG. 7, a wafer 40 including the substrate 4 is prepared, and a nanoimprinting resin 50 is arranged on a surface 40a of the wafer 40. For example, UV-curable resins (such as resins based on acrylics, fluorine, epoxy, silicone, and urethane and inorganic/organic hybrid materials) can be used as the nanoimprinting resin 50.

Subsequently, as illustrated in (b) of FIG. 7, while the replica mold. R is pressed against the nanoimprinting resin 50 on the wafer 40, the nanoimprinting resin 50 is cured by irradiation with UV, for example, so as to transfer the pattern of the replica mold R to the nanoimprinting resin 50. This forms the molded layer 5 having a pattern (i.e., the pattern of the master mold M) which is the reverse of the pattern of the replica mold R. Adjusting parameters such as the viscosity of the nanoimprinting resin 50 and the pressure on the replica mold R at this time can form the support part 7. Then, as illustrated in (c) of FIG. 7, the replica mold R is released from the molded layer 5.

Here, the nanoimprinting process illustrated in (a) to (c) of FIG. 7 may be performed such as to form a plurality of molded layers 5 collectively on a wafer level by using the replica mold R in a wafer size, or a plurality of molded layers 5 may be formed sequentially by repeatedly using the replica mold R having a size smaller than that of the wafer (step & repeat).

Performing the nanoimprinting step on the wafer level is accompanied with a dicing step for cutting out the substrate 4 (SERS element 3) as will be explained later. In this case, the dicing can be performed in an area provided as a dicing line where the substrate 4 is exposed between the frames 9 on the substrates 4 adjacent to each other, where the frame part 9 becomes relatively thin, or the like. This can prevent the frame part 9 from peeling due to the damage at the time of blade dicing, for example.

When forming the molded layer 5, the pattern of the master mold M may be transferred directly to the nanoimprinting resin 50 without using the film base. F. In this case, the steps for making the replica mold R illustrated in FIG. 6 are omitted, and the replica mold R in FIG. 7 becomes the master mold M.

The subsequent step vapor-deposits a conductor such as a metal (Au, Ag, Al, Cu, Pt, or the like) on the molded layer 5, so as to form the conductor layer 6, thereby constituting the optical function part 10. This constructs the SERS element 3. Then, as mentioned above, the wafer 40 is diced into the SERS elements 3, and the cut SERS element 3 is secured to the handling board 2, so as to yield the SERS unit 1.

In the SERS element 3 in accordance with this embodiment, as explained in the foregoing, the fine structure part 8 including the pillars 81 is formed integrally with the support part 7 extending along the front face 4a of the substrate 4. As a consequence, the fine structure part 8 is joined to the substrate 4 with the support part 7, whereby the fine structure part 8 (pillar 81) is restrained from peeling from the substrate 4. When a minute pillar is formed on the substrate separately and independently from the substrate, by contrast, the joint area between the pillar and substrate is so small that the pillar and substrate may easily peel from each other due to external physical forces such as vibrations and shocks and internal forces such as thermal impact.

When the fine structure part 8 is formed integrally with the support part 7 extending along the front face 4a of the substrate 4 as in the SERS element 3 in accordance with this embodiment, a damage to a part of the substrate 4 may affect the whole fine structure part 8 through the support part 7, for example. Examples of causes of the damage to the substrate 4 seem to include chipping occurring when picking an end of the substrate 4 with tweezers and contact with collets at the time of mounting the substrate 4.

In the SERS element 3 in accordance with this embodiment, by contrast, the support part 7 and fine structure part 8 are surrounded by the frame part 9, whereby the damage is held by the frame part 9, so as not to affect the fine structure part 8. Therefore, the SERS element 3 in accordance with this embodiment can restrain the fine structure part 8 (pillars 81) from peeling and prevent the damage from affecting the fine structure part 8, thereby inhibiting reliability from lowering.

In the SERS element 3 in accordance with this embodiment, the support part 7 and frame part 9 define the recess C in the molded layer 5, while the fine structure part 8 is formed in the recess C. Therefore, a fixed amount of the solution sample 12 can be reserved in the region formed with the fine structure part 8 (within the recess C), so as to improve efficiency in adhesion of the sample 12 to the fine structure part 8 (to the conductor layer 6 on the fine structure part 8). For the same reason, the amount of the solution sample 12 can be made constant, so as to enhance reproducibility in Raman spectroscopic analysis.

In the SERS element 3 in accordance with this embodiment, the height H9 of the frame part 9 is greater than the height H8 of the fine structure part 8, so that Raman spectroscopic analysis can be conducted with the glass cover 13 mounted on the frame part 9. This enables the analysis to be performed while protecting the fine structure part 8 (hindering impurities from mingling) and preventing the solution from evaporating. The distance between the arranged glass cover 13 and the fine structure part 8 can be kept constant among different elements, so as to achieve stable measurement (suppress fluctuations in measurement caused by variations in distance). Arranging the flat glass cover 13 can suppress the lens effect of the solution sample, thereby enabling appropriate measurement.

In the SERS element 3 in accordance with this embodiment, the frame part 9 can be used as a space for providing an alignment mark for mounting or a space to be marked for identifying chips. Chipping, if any, occurring in the SERS element 3 stops at the frame part 9, thereby avoiding an effective area including the fine structure part 8 from being damaged.

In the SERS element 3 in accordance with this embodiment, the support part 7, fine structure part 8, and frame part 9 can be constructed by integral molding, which makes it possible to save the step of separately making the individual parts and assembling them, and no alignment is necessary at the time of assembling.

In the SERS element 3 in accordance with this embodiment, the individual parts of the molded layer 5 are not bonded/joined to each other, whereby the solution sample 12 does not leak out of boundaries between the individual parts of the molded layer 5.

The foregoing embodiment explains only one mode of the surface-enhanced Raman scattering element. Therefore, the present invention is not limited to the above-mentioned SERS element 3, but may encompass any modifications of the SERS element 3 within the scope not altering the gist of each claim.

Figure 8:
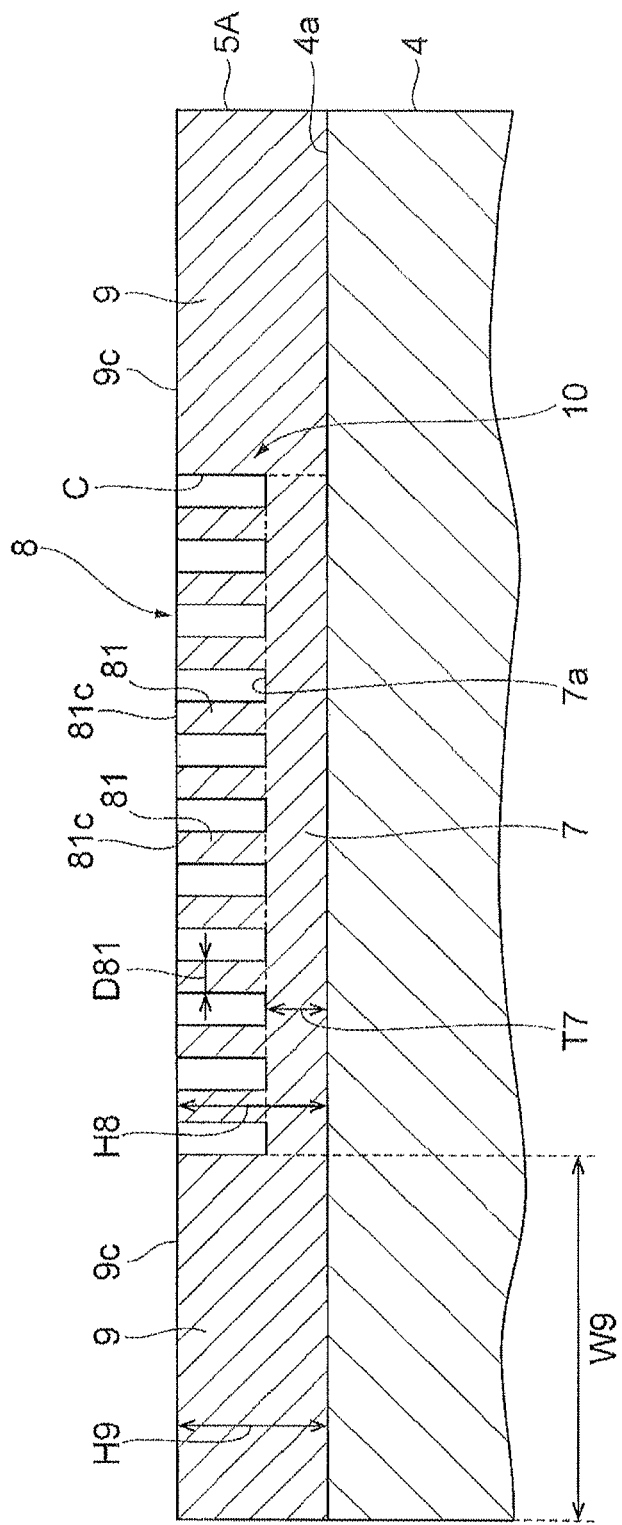
FIG. 8 is a schematic enlarged sectional view illustrating a modified example of the molded layer depicted in FIG. 3.

For example, the SERS element 3 may comprise the modified layer 5A illustrated in FIG. 8 in place of the molded layer 5. The molded layer 5A differs from the molded layer 5 in that the height H9 of the frame part 9 and the height H8 of the fine structure part 8 are substantially the same. The molded layer 5A like this can be formed as in the case of forming the molded layer 5 by the above-mentioned nanoimprinting, for example. In addition to the effects mentioned above, the SERS element 3 equipped with the molded layer 5A like this can exhibit the following effects when forming the molded layer 5A by nanoimprinting. These effects will be explained with reference to FIG. 9.

FIG. 9 is a diagram illustrating a part of steps of forming the molded layer depicted in FIG. 8 by nanoimprinting. In FIG. 9, (a) illustrates a state where a nanoimprinting resin is cured while the replica mold R is pressed against it, so as to form the molded layer 5A. In FIG. 9, (b) illustrates a state where the replica mold R is released from the molded layer 5A. The area of a contact surface S between the replica mold R and the frame part 9 at an end part 8e of the fine structure part 8 is smaller (i.e., the surface energy is lower) in the molded layer 5A, in which the height H9 of the frame part 9 and the height H8 of the fine structure part 8 are substantially the same, than in the case where the height H9 of the frame part 9 is greater than the height H8 of the fine structure part 8 (e.g., the molded layer 5).

Therefore, when releasing the replica mold R from the molded layer 5 as illustrated in (b) of FIG. 9, both structures of the replica mold R and frame part 9 can be restrained from being damaged at the end part 8e of the fine structure part 8. Further, the molded layer 5A whose frame part 9 is thinner than the frame part 9 of the molded layer 5, for example, can make the amount of use of the nanoimprinting resin relatively smaller.

The height H9 of the frame part 9 may be made smaller than the height H8 of the fine structure part 8, and the above-mentioned effects at the time of formation seem to be obtained in this case as in the molded layer 5A. From the viewpoint of protecting the fine structure part 8, however, it is desirable for the height H9 of the frame part 9 to be the height H8 of the fine structure part 8 or greater. Therefore, making the height H9 of the frame part 9 and the height H8 of the fine structure part 8 substantially the same as in the molded layer 5A can achieve both of the above-mentioned effects during formation and the protection of the fine structure part 8.

Thus, in the SERB element 3, appropriately adjusting the height H9 of the frame part 9 can change the capacity of the recess C formed by the frame part 9 and support part 7, so as to regulate the maximum capacity for the solution sample 12. When the height H9 of the frame part 9 is smaller than the height H8 of the fine structure part 8, the frame part 9 surrounds a part of the fine structure part 8 on the support part 7 side and the support part 7 along the front face 4a of the substrate 4.

Here, the inventors have attained the following findings concerning the thicknesses (heights) of individual parts in the molded layer 5. That is, when the thickness T7 of the support part 7 located under the fine structure part 8 is made smaller, the deformation caused by thermal expansion decreases, thereby becoming less influential in changes in characteristics. This is because of the fact that, since the stretching of a resin or the like by thermal expansion is obtained by multiplying its thickness, the coefficient of thermal expansion of its material, and the change in temperature, the absolute value of expansion caused by thermal expansion can be lowered when the thickness is made smaller. On the other hand, increasing the thickness of the frame part 9 (height H9) acts to mitigate the distortion caused by its difference in coefficient of thermal expansion from the substrate 4, whereby it can be prevented from peeling from the substrate 4 and so forth.

According to such findings by the inventors, it is preferable for the thicknesses and the like of individual parts of the molded layer 5 to be set so as to satisfy at least one of (width W9 of the frame part 9)>(thickness T7 of the support part 7), (width W9 of the frame part 9)>(column diameter D81 of the pillar 81), (width W9 of the frame part 9)>(height H9 of the frame part 9), and (height H9 of the frame part 9)>(thickness T7 of the support part 7), for example.

The frame part 9, which is integrally formed with the support part 7 as the molded layer 5 in the above-mentioned embodiment, may be constructed separately from the support part 7. In particular, the frame part 9 may be constituted by an elastic material. This enables the frame part 9 to hold the damage to a part of the substrate 4 securely, for example.

The conductor layer 6 is not limited to the one directly formed on the molded layer 5 (fine structure part 8), but may be formed indirectly on the molded layer 5 (fine structure part 8) with a layer such as a buffer metal (Ti, Cr, or the like) for improving the adhesion of a metal to the molded layer 5 (fine structure part 8), for example, interposed therebetween.

Without being restricted to those mentioned above, various materials and forms can be employed for the above-mentioned constituents of the SERB element 3.

Figure 10:
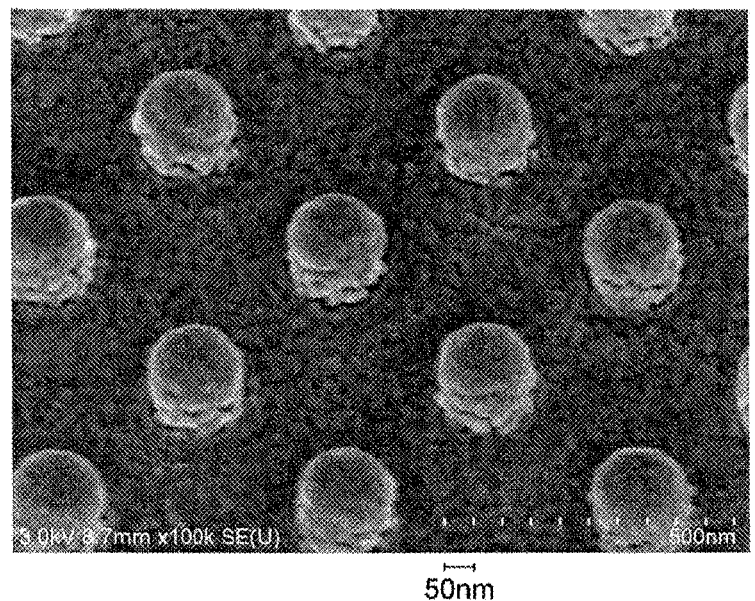
FIG. 10 is a photograph of an optical function part of a surface-enhanced Raman scattering unit.

The optical function part shown in FIG. 10 is one in which Au was vapor-deposited as a conductor layer so as to yield a thickness of 50 nm in a fine structure part made of a nanoimprinting resin having a plurality of pillars (each having a diameter of 120 nm and a height of 180 nm) periodically arranged at a predetermined pitch (center line distance of 360 nm).

INDUSTRIAL APPLICABILITY

One aspect of the present invention can provide a surface-enhanced Raman scattering element which can inhibit reliability from lowering.

REFERENCE SIGNS LIST

1: SERS unit (surface-enhanced Raman scattering unit); 3: SERS element (surface-enhanced Raman scattering element); 4: substrate; 4a: front face (principal surface); 5: molded layer; 6: conductor layer; 7: support part; 8: fine structure part; 9: frame part; 10: optical function part; 81: pillar.

The invention claimed is:

1. A surface-enhanced Raman scattering element comprising:
   a substrate having a principal surface;
   a molded layer having a support part formed on the principal surface of the substrate so as to extend along the principal surface and a fine structure part formed on the support part;
   a frame part formed on the principal surface of the substrate so as to surround the support part and fine structure part along the principal surface; and
   a conductor layer formed on at least the fine structure part and constituting an optical functional part for generating surface-enhanced Raman scattering;
   wherein the fine structure part is formed integrally with the support part,
   wherein a front surface of the support part is formed integrally with the fine structure part, and a rear surface of the support part is joined to the principal surface of the substrate,
   wherein the fine structure part includes a plurality of pillars, a thickness of the support part from a front face of the substrate being larger than a column diameter of at least one of the plurality of pillars, a height of at least one of the plurality of pillars being larger than the column diameter of at least one of the plurality of pillars,
   wherein the conductor layer reaches the surfaces of the plurality of pillars and a surface of the support part exposed between the plurality of pillars,
   wherein the conductor layer is formed on both top surfaces of the pillars and the surface of the support part exposed between the pillars.

2. The surface-enhanced Raman scattering element according to claim 1, wherein the frame part is formed integrally with the support part as the molded layer.

3. The surface-enhanced Raman scattering element according to claim 1, wherein the frame part has a height from the principal surface of the substrate greater than that of the fine structure part from the principal surface of the substrate.

4. The surface-enhanced Raman scattering element according to claim 1, wherein the frame part is constituted by an elastic material.

5. The surface-enhanced Raman scattering element according to claim 1, wherein the fine structure part includes the plurality of pillars erected on the support part; and
   wherein the plurality of pillars are formed integrally with the support part and connected to each other.

6. The surface-enhanced Raman scattering element according to claim 5, wherein, in a direction along the principal surface of the substrate, the frame has a width greater than a thickness of the pillar.

7. The surface-enhanced Raman scattering element according to claim 1, wherein the conductor layer is formed over the fine structure part and frame part.

* * * * *